United States Patent [19]
Matsumura

[11] Patent Number: 5,065,436
[45] Date of Patent: Nov. 12, 1991

[54] X-RAY COMPUTERIZED TOMOGRAPH

[75] Inventor: Shigeru Matsumura, Tokyo, Japan

[73] Assignee: Yokogawa Medical Systems, Limited, Tokyo, Japan

[21] Appl. No.: 474,105

[22] PCT Filed: Oct. 31, 1988

[86] PCT No.: PCT/JP88/01113

§ 371 Date: Apr. 17, 1990

§ 102(e) Date: Apr. 17, 1990

[87] PCT Pub. No.: WO89/03658

PCT Pub. Date: May 5, 1989

[30] Foreign Application Priority Data

Oct. 30, 1987 [JP] Japan .................. 62-275181

[51] Int. Cl.$^5$ .............................................. G06K 9/00
[52] U.S. Cl. ................................ 382/6; 364/413.14; 364/413.17; 364/413.19
[58] Field of Search ............. 382/6, 54; 364/413.13, 364/413.14, 413.16, 413.17, 413.19, 413.22; 378/62, 21

[56] References Cited

U.S. PATENT DOCUMENTS

| | | | |
|---|---|---|---|
| 4,707,786 | 11/1987 | Dehner | 382/6 |
| 4,731,865 | 3/1988 | Sievenpiper | 382/54 |
| 4,903,205 | 2/1990 | Hishinuma | 382/6 |
| 4,903,310 | 2/1990 | Takeo et al. | 364/413.13 |
| 4,947,323 | 8/1990 | Smith | 364/413.13 |
| 4,975,970 | 12/1990 | Zettel et al. | 382/6 |

FOREIGN PATENT DOCUMENTS 52-104890 9/1977 Japan .
62-47346 3/1987 Japan .

Primary Examiner—David K. Moore
Assistant Examiner—Joseph Mancuso
Attorney, Agent, or Firm—Moonray Kojima

[57] ABSTRACT

In an X-ray CT which extracts data corresponding to transmitted data of a parallel beam X-ray from transmitted data of an X-ray acquired based on a fan beam X-ray and carries out reconstruction of an image based on the data, the present invention which removes shower-shaped artifacts generated in a reconstructed image by influences of an instantaneous change in strength of an X-ray is characterized in storing output data of a data acquisition device corresponding to a plurality of views in a buffer memory, forming view data from which the influences of a variation in strength of an X-ray are removed by weighted averaging the data corresponding to a plurality of views stored in the buffer memory, and replacing view data at the time when a variation in strength of an X-ray is present with the view data.

4 Claims, 2 Drawing Sheets 5,065,436

X-RAY COMPUTERIZED TOMOGRAPH

TECHNICAL FIELD

The present invention relates to removement of artifacts in a reconstructed image in an X-ray computerized tomograph which extracts data corresponding to transmitted data of a parallel beam X-ray from transmitted data of an X-ray acquired based on a fan beam X-ray and reconstructs an image based on the data.

BACKGROUND ART

An X-ray computerized tomograph (hereinafter, called as an X-ray CT) is a device which reconstructs a tomogram image of a body under test from transmitted data of an X-ray obtained by irradiating an X-ray from the circumference of a body under test. An X-ray CT of a ROTATE - ROTATE system irradiates a fan beam X-ray on a body under test and detects the strength of an X-ray which transmits the body under test by use of a multi-channel X-ray detector. Accordingly, view data obtained by one irradiation become fan beam data. As one of methods of reconstructing an image based on such the view data, there is known a method in which parallel beam data are extracted from fan beam data, and an image reconstructing algorithm for a parallel beam is applied to the parallel beam data. In that case, data based on beams which are parallel with each other are picked up from fan beam data having different views with each other, thereby forming parallel beam data for each view. Therefore, data in each channel in one view have the time of irradiation of an X-ray which is different for each channel. Accordingly, in the case where an X-ray source generates, for example, a ripple-shaped output variation, data for one view include influences of such the X-ray output variation in the channel direction. The influences of such the X-ray output variation can be removed by carrying out acquisition of data in the reference channel of an X-ray detector with a sufficiently fine sampling period and carrying out correction of view data using the data in the reference channel. But, this is not effective in the case where an X-ray output decreases instantaneously due to an abnormal discharge occurring in an X-ray tube and so forth, and shower-shaped artifacts occur on the reconstructed image due to the influence of the above-mentioned decrease of the output.

SUMMARY OF THE INVENTION

It is an object of the present invention to remove shower-shaped artifacts generated in a reconstructed image due to influences of an instantaneous change in strength of an X-ray in an X-ray CT which extracts data corresponding to transmitted data of a parallel beam X-ray from transmitted data of an X-ray acquired based on a fan beam X-ray and reconstructs an image based on the data.

The present invention is characterized in that data corresponding to a plurality of views among output data of a data acquisition device are stored in a buffer memory, view data in which the influences of a variation in strength of an X-ray have been removed are formed by weighted averaging the data corresponding to a plurality of views stored in the buffer memory, and view data at the time when a variation in strength of an X-ray was present ar replaced with the view data.

BEST MODE FOR CARRYING OUT THE INVENTION

Figure 1:
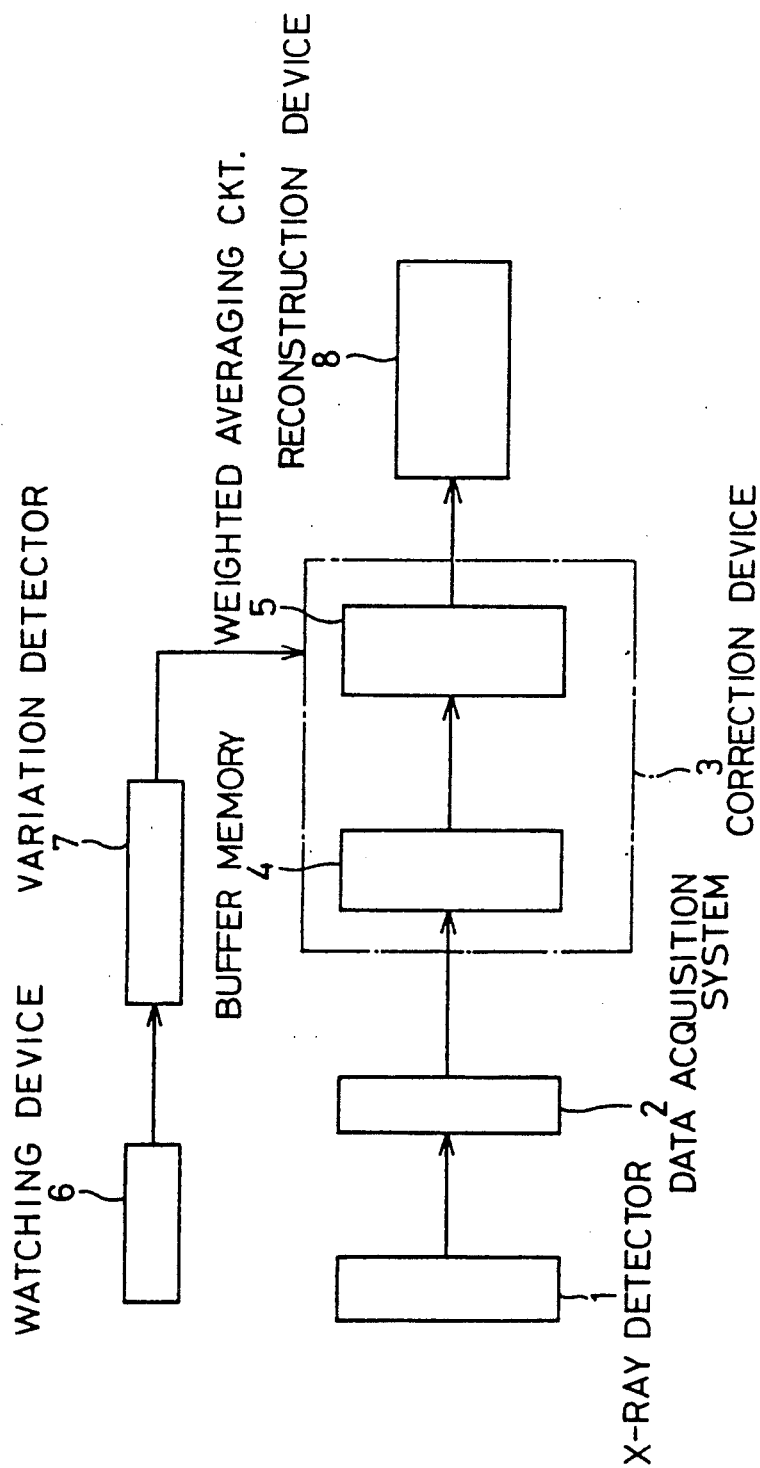
FIG. 1 is a conceptual constitution diagram of an embodiment according to the present invention.

In FIG. 1, reference numeral 1 is a multi-channel X-ray detector for detecting a fan beam X-ray which is irradiated from an X-ray tube (not shown) to transmit a body under test (not shown) and outputting a signal proportional to strength of a X-ray, and 2 is a data acquisition device which converts output signals of the multi-channel of the X-ray detector 1 into a digital signal and then acquires them. The X-ray detector 1 and the data acquisition device 2 are both same as those usually used in an X-ray CT. Reference numeral 3 is a correction device which forms a feature of the present invention and includes a buffer memory 4 and a weighted averaging circuit 5. Output data corresponding to a plurality of views among output data of the data acquisition device 2 are stored in the buffer memory 4 in the correction device 3, the data in the buffer memory 4 are processed by the weighted averaging circuit 5. Reference numeral 6 is a watching device which always watches a voltage or a current supplied to an X-ray tube and produces an output signal proportional to the voltage or the current in an X-ray generation system such as an X-ray tube and so forth. Incidentally, as the watching device 6, there may be a device which watches strength of an X-ray directly. Reference numeral 7 is a variation detector which receives the output signal of the watching device 6 and detects an abnormal variation in strength of an X-ray. The variation detector 7 has a reference value for the output signal of the watching device 6, obtains a ratio of the watched output in the n-th view to the reference value, and judges the output signal to be abnormal or normal depending on whether or not the ratio is not more than a fixed value. Further, the variation detector 7 adopts the value of the watched output in the n-th view which it has judged to be normal as a new reference value for a watched output in the (n+1)-th view. Incidentally, the variation detector 7 may be a device which extracts only a sudden change by making the output signal of the watching device 6 pass through a highpass filter, and compares the sudden change with a fixed reference value for judgement. The judged output signal of the variation detector 7 is provided to the correction circuit 3 as a signal which controls the right or the wrong of a correcting operation. The correcting operation of the correction device 3 is made effective by an output signal judged to be abnormal from the variation detector 7 and ineffective by an output signal judged to be normal. When the operation is made effective, the correction device 3 outputs data obtained by applying such weighted averaging as shown described later to the data in the buffer memory 4 by the weighted averaging circuit 5, and when the operation is made ineffective, the correction device 3 outputs the output data of the data acquisition device 2 as it is. Such the output data of the correction device 3 are input to a reconstruction device 8. The reconstruction device 8 extracts parallel beam data from fan beam data, and carries out image reconstruction for the parallel data. Such the reconstruction device has been already known.

The operation of the X-ray CT constructed as described above is as follows. An X-ray which transmits a body under test is detected by the X-ray detector 1, acquired as digital view data in the data acquisition device 2, and input to the correction device 3. In the correction device 3, the input view data are stored in the buffer memory 4 for each view. On the other hand, the watching device 6 always watches a voltage, a current, or strength of an X-ray itself which is supplied to an X-ray tube and supplies a watched signal proportional to the above one to the variation detector 7. The variation detector 7 compares the watched output signal with the reference value, judges the presence or absence of abnormality in an X-ray source, and generates a judged output signal for representing the judgement. While the variation detector 7 outputs an output signal judged to be normal, the correction device 3 does not function, and the output data of the data acquisition device 2 is provided to the reconstruction device 8 as they are. When the variation detector 7 outputs an output signal judged to be abnormal, the correction device 3 functions, and carries out such weighted averaging as described in the following using data of a plurality of views stored in the buffer memory 4 by the weighted averaging circuit 5. In other words, assuming that some abnormality occurs at the j-th view, the weighted averaging circuit 5 reads out data of ±L views before and after the data of the j-th view including the data of the j-th view from the buffer memory 4, that is, data of the (2L+1) views in total and carries out the following calculation. Moreover, this calculation is carried out for data before normalization.

$$C(i,j) = \sum_{k=-L}^{L} W_k \cdot D(i,j+k) \quad (1)$$

where
i: channel number
j: view number
L: the number of the views before and after used for correction
$W_k$: weight coefficient assigned for each channel
D (i,j): data before correction
C (i,j): data after correction The expression (1) represents that the data after correction of the i channel of the j view in which some abnormality in strength of X-ray occurs are obtained by weighted averaging the data of the same i channel in the j view and the ±L views before and after the j view.

As a concrete example, assuming that the following expressions, that is, the number of views L before and after the j view L=1, the weight coefficient $W_{-1}=1$, $W_0=2$, and $W_1=1$ hold, the corrected data C (i,j) can be obtained as shown in the following.

$$C(i,j) = D(i,j-1) + 2D(i,j) + D(i,j+1)$$

Figure 2A:
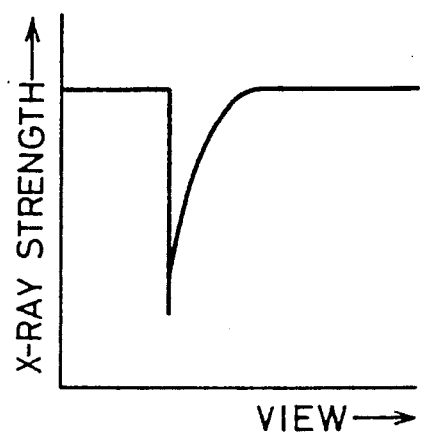
FIGS. 2a and b are diagrams explanatory of correction of data using an embodiment according to the present invention.
Figure 2B:
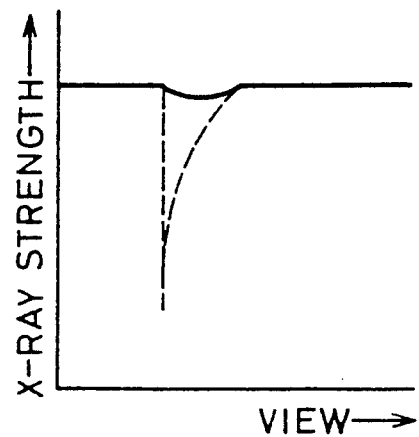

According to such the correction, view data subjected to influences of an instantaneous change in strength of an X-ray as shown in FIG. 2A are corrected to view data from which the influences of a change in strength of an X-ray are removed as shown in FIG. 2B. The corrected data are input into the reconstruction device 8 as new data of j views. The reconstruction device 8 reconstructs an image for the view data obtained in this way. At this time, a reconstructed image for the view data employed for the reconstruction does not include shower-shaped artifacts, because the influences of an instantaneous variation in strength of an X-ray have been removed even if the above-mentioned instantaneous variation has been present.

Though the best mode for carrying out the present invention has been stated in the above-mentioned description, it is easy for a person having ordinary knowledge in the field of the art to which the present invention belongs to prepare various kinds of modifications without departing from the claims described below.

What is claimed is:

1. In an X-ray CT comprising
   a multi-channel detector for detecting a fan beam X-ray which is transmitted through a body under test; and
   a data acquisition device for acquiring view data based on an output signal from said multi-channel detector;
   the improvement comprising means for removing artifacts in a reconstructed image caused by instantaneous changes in strength of the X-ray, said means comprising
   watching means for watching the instantaneous strength of output from an X-ray source directly or indirectly;
   variation detecting means for detecting an abnormal variation in the instantaneous strength of the output from said X-ray source, by comparing an output signal from said watching means with a reference value;
   correction means comprising
      buffer memory means for storing output data from said data acquisition device corresponding to a plurality of views, and
      weighted averaging means for forming corrected view data by weighted averaging said data corresponding to a plurality of views stored in said buffer memory means, said correction means under control of an output signal from said variation detecting means for producing output data obtained from said data acquisition device, without any change, when the output data from said variation detecting means does not represent an abnormal variation in the instantaneous strength of the output from said X-ray source, and for producing output data which is corrected by weighted averaging of data stored in said buffer memory means corresponding to a plurality of views, when the output signal from said variation detecting means represents an abnormal variation in the instantaneous strength of the output from said X-ray source; and
   reconstruction means for receiving view data from said correction means, and for extracting parallel beam data from fan beam data, thereby carrying out image reconstruction for a parallel beam with artifacts due to instantaneous changes in the strength of X-rays being removed.

2. The X-ray CT according to claim 1, wherein said watching means watches a voltage supplied to an X-ray tube.

3. The X-ray CT according to claim 1, wherein said watching means watches a current supplied to an X-ray tube.

4. The X-ray CT according to claim 1, wherein said watching means watches strength of an X-ray which said X-ray tube generates.

* * * * *